(12) United States Patent
Filliers et al.

(10) Patent No.: US 7,524,961 B2
(45) Date of Patent: Apr. 28, 2009

(54) DIASTEREOSELECTIVE ADDITION OF LITHIATED N-METHYLIMIDAZOLE ON SULFINIMINES

(75) Inventors: Walter Ferdinand Maria Filliers, Vremde (BE); Rudy Laurent Maria Broeckx, Turnhout (BE); Patrick René Angibaud, Fontaine-Bellenger (FR)

(73) Assignee: Janssen Pharmaceutica, N.V., Beerse (BE)

( * ) Notice: Subject to any disclaimer, the term of this patent is extended or adjusted under 35 U.S.C. 154(b) by 75 days.

(21) Appl. No.: 11/568,415

(22) PCT Filed: Apr. 28, 2005

(86) PCT No.: PCT/EP2005/051928

§ 371 (c)(1),
(2), (4) Date: Oct. 27, 2006

(87) PCT Pub. No.: WO2005/105782

PCT Pub. Date: Nov. 10, 2005

(65) Prior Publication Data

US 2007/0293679 A1 Dec. 20, 2007

(30) Foreign Application Priority Data

May 3, 2004 (EP) .................. 04076320

(51) Int. Cl.
*C07D 215/12* (2006.01)
*C07D 215/00* (2006.01)
(52) U.S. Cl. ...................... 546/168; 546/157
(58) Field of Classification Search .............. 546/157, 546/168
See application file for complete search history.

(56) References Cited

FOREIGN PATENT DOCUMENTS

| WO | WO 97/21701 A | 6/1997 |
|---|---|---|
| WO | WO 01/53289 A | 7/2001 |
| WO | WO 02/072574 | 9/2002 |

OTHER PUBLICATIONS

Shapiro, G., et al. "Carboxylate Protection for the Synthesis of 4,5-Disubstituted 1-Methylimidazoles", J. Org. Chem. 1994. vol. 59, pp. 5524-5526.
Shapiro, G., et al. Synthesis of 2,5-Dilithio-1-Methylimidazole, Tetrahedron Letters. vol. 34, No. 21, pp. 3401-3404, 1993.
Shaw, A. W., et al. "Asymmetric synthesis of alpha,alpha-diaryl and alpha-aryl-alpha-heteroaryl alkylamines by organometallic additions to N-tert-butanesulfinyl Ketimines"., Tetrahedron Letters 42, (2001) 7173-7176.
International Search Report mailed Feb. 9, 2005 for PCT/EP2005/051928.

*Primary Examiner*—D. Margaret Seaman
*Assistant Examiner*—Nizal S Chandrakumar

(57) ABSTRACT

A diastereoselective synthesis process for the preparation of (R)-(+)-6-[amino(4-chlorophenyl) (1-methyl-1H-imidazol-5-yl)methyl]-4-(3-chlorophenyl)-1-methyl-2 (1H)-quinolinone which comprises the preparation of a compound of formula (VIII)

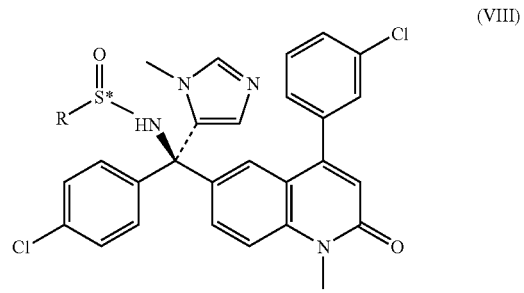

and the stereochemically isomeric forms thereof wherein R is $C_{1-6}$alkyl or $C_{1-6}$alkylphenyl-.

8 Claims, No Drawings

DIASTEREOSELECTIVE ADDITION OF LITHIATED N-METHYLIMIDAZOLE ON SULFINIMINES

CROSS REFERENCE TO RELATED APPLICATIONS

This application is the national stage of Application No. PCT/EP2005/051928, filed Apr. 28, 2005, which claims priority from EPO Patent Application No. 04076320.3, filed May 3, 2004, the entire disclosures of which are hereby incorporated in their entirely.

The present invention relates to the diastereoselective synthesis process of 5-substituted imidazole compounds which have farnesyl tranferase inhibitory activity and to compounds used in the synthesis process for said imidazole compounds.

Farnesyltransferase inhibitors block the main post-translational modification of the Ras protein, thus interfering with its localization to the inner surface of the plasma membrane and subsequent activation of the downstream effectors. Although initially developed as a strategy to target Ras in cancer, farnesyltransferase inhibitors have subsequently been acknowledged as acting by additional and more complex mechanisms that may extend beyond Ras involving GTP-binding proteins, kinases, centromere-binding proteins and probably other farnesylated proteins.

A particular farnesyltransferase inhibitor is described in WO 97/21701, namely (R)-(+)-6-[amino(4-chlorophenyl)(1-methyl-1H-imidazol-5-yl)methyl]-4-(3-chlorophenyl)-1-methyl-2(1H)-quinolinone. The absolute stereochemical configuration of the compound was not determined in the experiments described in the above-mentioned patent specification, but the compound was identified by the prefix "(B)" to indicate that it was the second compound isolated from column chromatography. The compound thus obtained has been found to have the (R)-(+)-configuration. This compound will be referred to below by its published code number R115777 and has the following formula (V).

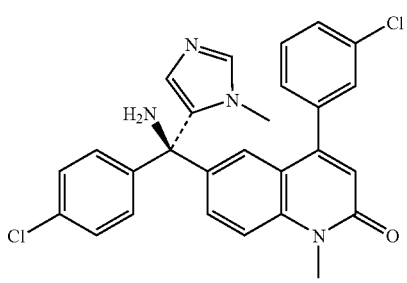

(V)

R115777 (Tipifarnib) is a potent, orally active inhibitor of farnesylprotein transferase. It is one of the most advanced of the farnesylprotein transferase inhibitors currently reported to be in clinical development, being one of the agents that have progressed to phase III studies.

R115777 has been found to have very potent activity against neoplastic diseases. Antineoplastic activity in solid tumors, such as breast cancer, as well as in haematological malignancies, such as leukemia, have been observed. Also combination studies have been carried out demonstrating that R115777 can be safely combined with several highly active anticancer drugs.

In WO 01/53289, the racemates (±) (4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one (racemate 1) and (±) 4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one (racemate 2) are prepared.

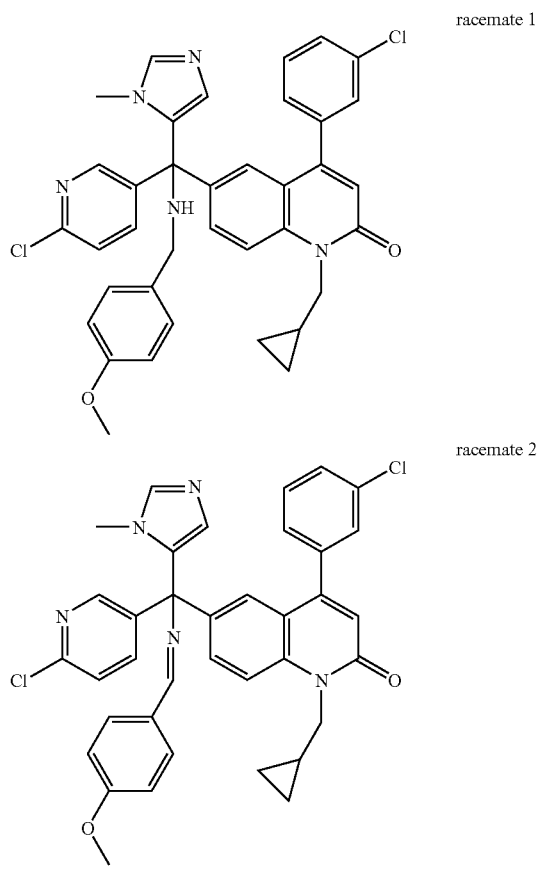

After chiral molecule separation using column chromatography, either the benzylamino or the benzilidine moiety of the resulting (+) and/or (−) enantiomers are converted to an amino group under acidic conditions.

The synthesis of R115777 as originally described in WO 97/21701, is presented in scheme 1.

Herein, in step 1, the intermediate 1-methyl imidazole in tetrahydrofuran, is mixed with a solution of n-butyllithium in a hexane solvent to which is added chlorotriethylsilane (triethylsilyl chloride), followed by a further addition of n-butyllithium in hexane, the resulting mixture being cooled to −78° C. before the addition of a solution of a compound of formula (I), i.e. 6-(4-chlorobenzoyl)-4-(3-chlorophenyl)-1-methyl-2(1H)-quinolinone in tetrahydrofuran. The reaction mixture is subsequently brought to room temperature, and then hydrolysed, extracted with ethyl acetate and the organic layer worked up to obtain a compound of formula (II), i.e. (±)-6-[hydroxy(4-chlorophenyl)(1-methyl-1H-imidazol-5-yl)methyl]-4-(3-chlorophenyl)-1-methyl-2(1H)-quinolinone.

In step 2, the hydroxy compound of formula (II) is chlorinated with thionylchloride to form a compound of formula (III), i.e. (±)-6-[chloro(4-chlorophenyl)(1-methyl-1H-imidazol-5-yl)methyl]-4-(3-chlorophenyl)-1-methyl-2(1H)-quinolinone.

In step 3, the chloro compound of formula (III) is treated, with NH₄OH in tetrahydrofuran to form the amino compound of formula (IV), i.e. (±)-6-[amino(4-chlorophenyl)(1-methyl-1H-imidazol-5-yl)methyl]-4-(3-chlorophenyl)-1-methyl-2(1H)-quinolinone.

In step 4, the amino compound of formula (IV) is separated into its enantiomers by chiral column chromatography over Chiracel OD (25 cm; eluent: 100% ethanol; flow: 0.5 ml/min; wavelength: 220 nm). The pure (B)-fractions are collected and recrystallised from 2-propanol resulting in R115777, the compound of formula (V).

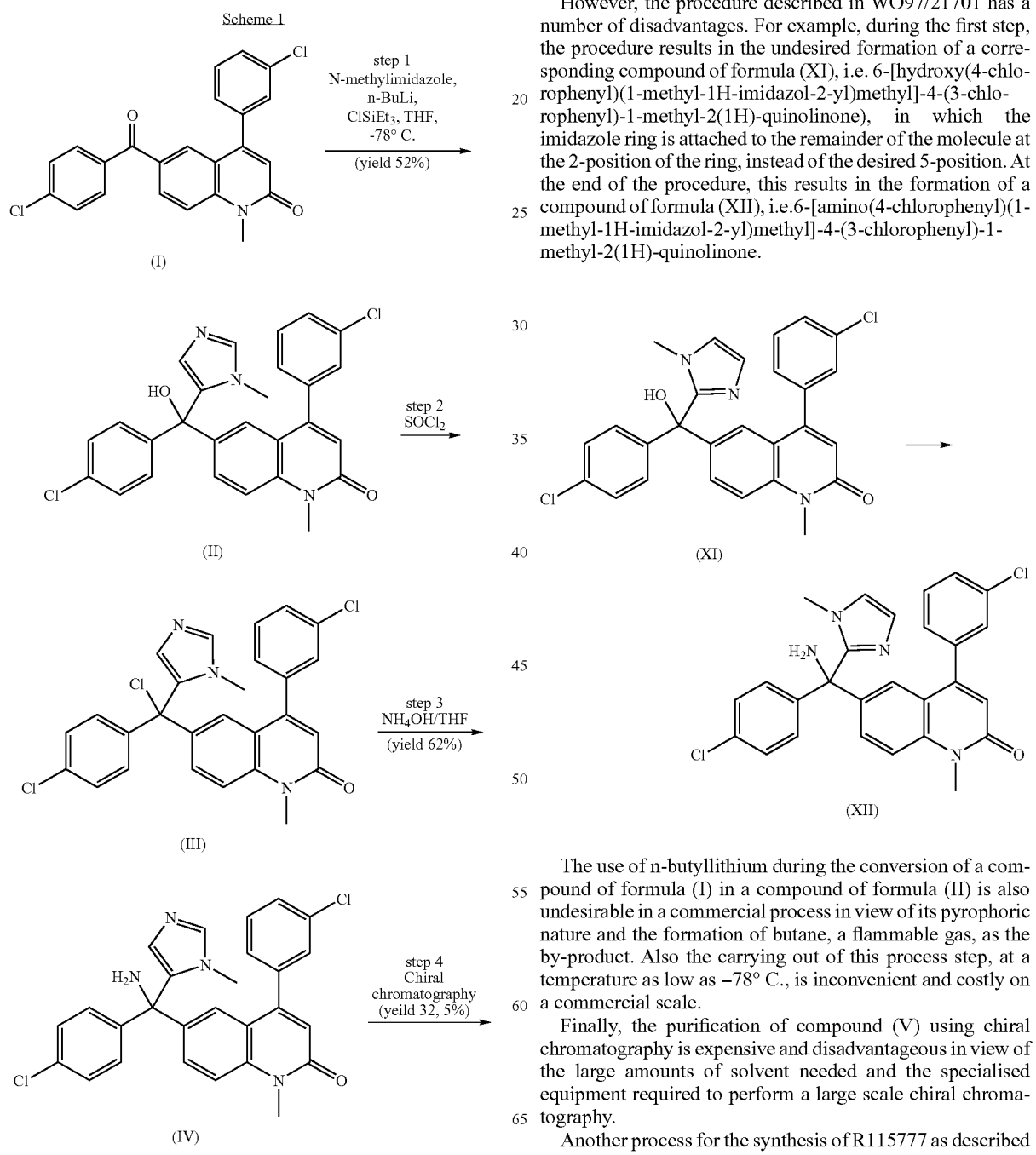

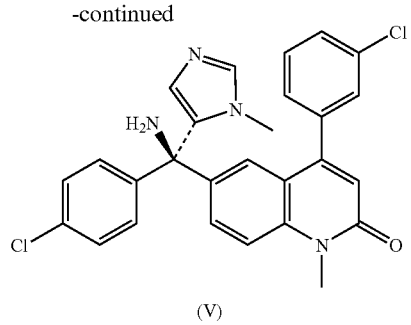

However, the procedure described in WO97/21701 has a number of disadvantages. For example, during the first step, the procedure results in the undesired formation of a corresponding compound of formula (XI), i.e. 6-[hydroxy(4-chlorophenyl)(1-methyl-1H-imidazol-2-yl)methyl]-4-(3-chlorophenyl)-1-methyl-2(1H)-quinolinone), in which the imidazole ring is attached to the remainder of the molecule at the 2-position of the ring, instead of the desired 5-position. At the end of the procedure, this results in the formation of a compound of formula (XII), i.e. 6-[amino(4-chlorophenyl)(1-methyl-1H-imidazol-2-yl)methyl]-4-(3-chlorophenyl)-1-methyl-2(1H)-quinolinone.

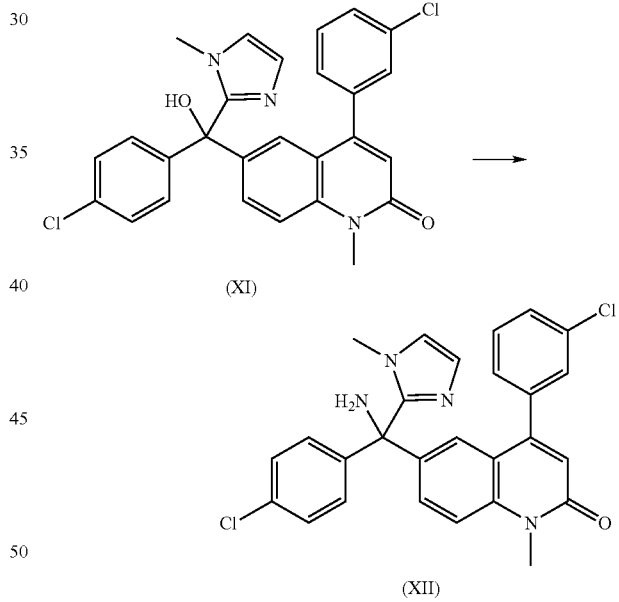

The use of n-butyllithium during the conversion of a compound of formula (I) in a compound of formula (II) is also undesirable in a commercial process in view of its pyrophoric nature and the formation of butane, a flammable gas, as the by-product. Also the carrying out of this process step, at a temperature as low as −78° C., is inconvenient and costly on a commercial scale.

Finally, the purification of compound (V) using chiral chromatography is expensive and disadvantageous in view of the large amounts of solvent needed and the specialised equipment required to perform a large scale chiral chromatography.

Another process for the synthesis of R115777 as described in WO 02/072574, is presented in scheme 2.

Herein, in step 1, 1-methyl imidazole in tetrahydrofuran is mixed with a solution of n-hexyllithium in a hexane solvent to which is added tri-iso-butylsilyl chloride, followed by a further addition of n-hexyllithium in hexane. The compound of formula (I) in tetrahydrofuran is then added to the reaction mixture, keeping the temperature between −5° C. and 0° C. The resulting product of formula (II) is isolated by salt formation.

In step 2, the chlorination reaction is effected by treatment of the compound of formula (II) with thionyl chloride in 1,3-dimethyl-2-imidazolidinone.

In step 3, the chloro compound of formula (III) is treated with a solution of ammonia in methanol. After the addition of water, the compound of formula (IV), precipitates and can be isolated.

In step 4, the compound of formula (IV) can be reacted with L-(−)-dibenzoyl tartaric acid (DBTA) to form the diastereomeric tartrate salt with formula (VI) i.e. R-(−)-6-[amino(4-chlorophenyl)(1-methyl-1H-imidazol-5-yl)methyl]-4-(3-chlorophenyl)-1-methyl-2(1H)-quinolinone [R-(R*,R*)]-2,3-bis(benzoyloxy)butanedioate (2:3).

Finally, in step 5, the compound of formula (VI) is treated with aqueous ammonium hydroxide, to form the crude compound of formula (V) which is then purified by recrystallisation from ethanol to the pure compound (V).

Scheme 2

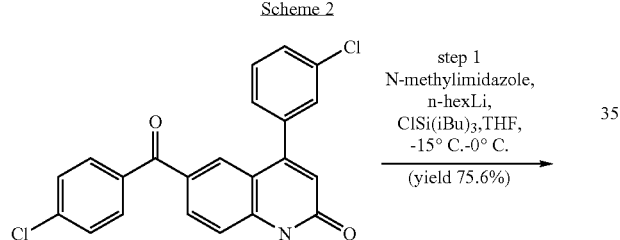

(I)

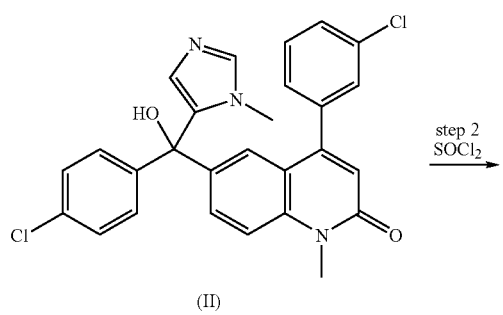

(II)

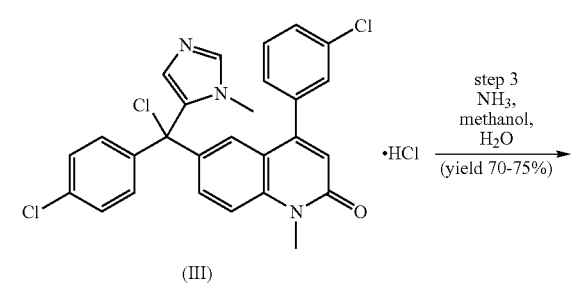

(III)

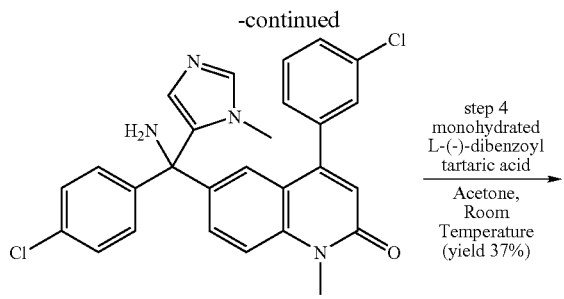

(IV)

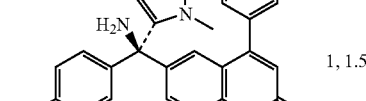

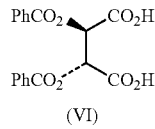

(VI)

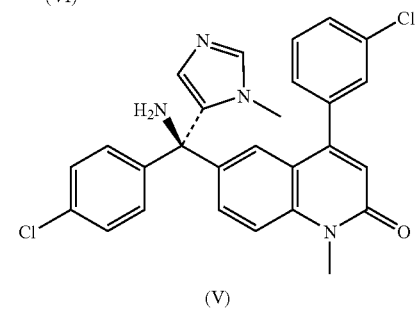

(V)

However, in view of the fact that water is present during the third and the fifth step of this procedure, there is significant formation of the hydroxy compound of formula (II).

This is important because the compounds of formula (II) and (V) are difficult to separate. In order to keep the quality of the final product (V) as high as possible, it is critical to limit the formation of compound (II).

The major drawback of the above described processes is the generation of large amounts of the other enantiomer that subsequently must be recycled.

Attempts were made to develop processes that solve this problem. One of the possibilities was to enter chirality in the first step of the procedure. A first study was carried out in order to determine if the conversion of an enantiomer of the hydroxy compound of formula (II) into a compound of formula (IV) could preserve chirality. Several experimental conditions have been tested starting with an enantiomer of a compound of formula (II), but racemisation always occurred.

Another possibility was to try entering chirality by adding N-methylimidazole under the reaction conditions described herein above under steps 1 of WO97/21701 and WO 02/072574, to an N—$C_{1-6}$alkyl-(S(R))-sulfinylketimine prepared from the compound of formula (I). It turned out that the resulting N—$C_{1-6}$alkyl-(S(R))-sulfinylamide of the compound of formula (I) was in the desired R-configuration and could be used for conversion into compound (V).

These results are completely unexpected, especially in view of Shaw et al. (Tetrahedron Letters: 42, 7173-7176).

Already in 2001, Shaw et al. disclosed an asymmetric synthesis process for the production of α-aryl-α-heteroaryl alkylamines using organometallic additions to N-tert-butanesulfinyl ketimines. However, the configuration and the yield of the final enantiomer formed with this process, was depending on the configuration of the N-tert-butanesulfinyl moiety of the ketimines, the composition of the aryl and/or the heteroaryl moieties of the ketimines, as well as on the organo- and the metallic moiety of the organometallic reagent. Furthermore, the use of heteroaryllithium reagents were described in this document, as being in particular disadvantageous, in view of their instability.

Thus the present invention solves the above described problems. It provides a new process for the preparation of the compound of formula (V) without the need to recycle one of the enantiomers while minimising the formation of undesired isomers and impurities and under conditions which offer economic advantages for operation on a commercial scale.

The present invention provides a process for the preparation of a compound of formula (VIII)

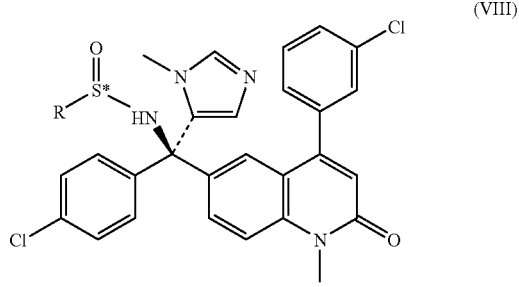

(VIII)

wherein R is $C_{1-6}$alkyl or $C_{1-6}$alkylphenyl- which comprises reacting a compound of formula (IX)

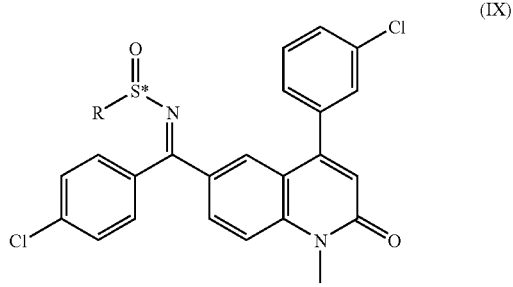

(IX)

wherein R is $C_{1-6}$alkyl or $C_{1-6}$alkylphenyl- with a $C_{4-6}$alkyllithium compound, 1-methylimidazole and a tri($C_{2-4}$alkyl) silyl halide.

As used in the foregoing definitions and hereinafter $C_{1-6}$alkyl defines straight and branched chain saturated hydrocarbon radicals having from 1 to 6 carbon atoms such as, e.g. methyl, ethyl, propyl, butyl, 1-methylethyl, 2-methylpropyl, pentyl, 2-methyl-butyl, hexyl, 2-methylpentyl and the like, $C_{4-6}$alkyl defines straight and branched chain saturated hydrocarbon radicals having from 4 to 6 carbon atoms such as, e.g. butyl, 2-methylpropyl, pentyl, 2-methyl-butyl, hexyl, 2-methylpentyl and the like, $C_{2-4}$alkyl defines straight and branched chain saturated hydrocarbon radicals having from 2 to 4 carbon atoms such as, e.g. ethyl, propyl, butyl, 1-methylethyl, 2-methylpropyl and the like.

(S(R)) in the chemical name of some compounds means that the sulfur-atom in the molecule is in the R-configuration and (S(S)) means that the sulfur-atom in the molecule is in the S-configuration.

In the above described process, the diastereomeric excess of a compound of formula (VIII) is generally 20% or higher, preferably higher than 60%, more preferably higher than 80%, most preferably higher than 94%. The two diastereomers can be further purified (from the other diastereomer) by standard techniques like crystallisation or chromatography.

After conversion of a compound of formula (VIII) into the enantiomer of formula (V), racemisation or formation of a compound of formula (II) does not appear. The enantiomers of formula (V) can be further purified (from the other enantiomer) by standard techniques, such as crystallisation.

The reaction is conveniently effected in an ethereal organic solvent, for example diethylether, tert-butyl methyl ether or more preferably tetrahydrofuran.

The $C_{4-6}$alkyllithium can be butyllithium especially n-butyllithium, more preferably hexyllithium, especially n-hexyllithium. The tri($C_{2-4}$alkyl)silyl halide can be triethylsilyl halide, more preferably a tributylsilyl halide, especially tri-iso-butylsilyl halide. The silyl halide is preferably a silyl chloride.

It is common general knowledge that diastereomeric excess is higher when a diastereoselective process is performed at low temperatures. Unexpectedly, in the present invention, the influence of temperature can be limited. The reaction can be performed between -78° C. and 0° C., preferably between -40° C. and 0° C., more preferably between -15° C. and 0° C. The carrying out of this process step, at a temperature between -15° C. and 0° C. is expedient on a commercial scale. Furthermore higher temperatures can provide an improved yield.

In addition, the use of a temperature between -15° C. and 0° C. during this process, in combination with n-hexyllithium and tri-iso-butylsilyl chloride can provide an improved C5:C2-isomer ratio, i.e. the ratio between the compound in which the imidazolyl group is attached to the remainder of the molecule at the C5-position and the corresponding compound attached at the C2-position. For example, when during the process, n-butyllithium is used in combination with triethylsilyl chloride at a temperature of -70° C., the resulting product can generally, in accordance with prior art procedures discussed above, have a C5:C2-isomer ratio of 95:5. However, at temperatures above -50° C. the formation of the C2-isomer when compared to the C5-isomer, will be favoured (see scheme 3).

scheme 3

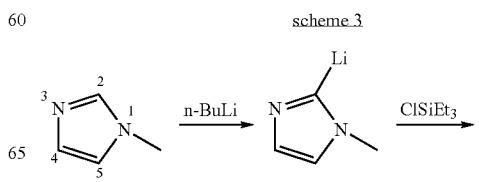

-continued

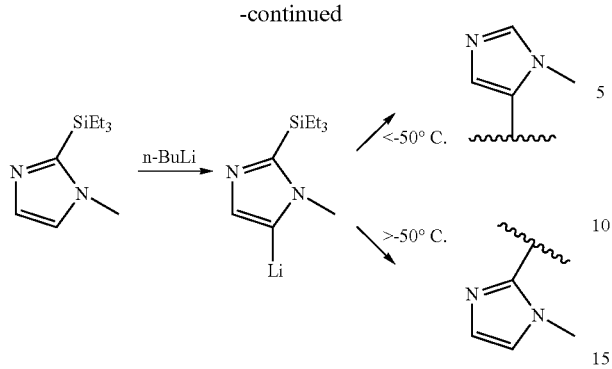

In contrast, when during the process, n-hexyllithium is used in combination with tri-iso-butylsilyl chloride at a temperature of −15° C. and 0° C., the resulting product can generally, in accordance with prior art procedures discussed above, have a C5:C2-isomer ratio of 99.8:0.2. This can be a significant difference on a commercial scale.

This selectivity at such relatively high temperatures is remarkable in view of suggestions in the literature that the silyl group is unsuitable as a blocking group, due to the 2- to 5-position migration of 2-(trialkylsilyl)-substituted 5-lithio-1-methylimidazoles (G. Shapiro and M. Marzi, Tetrahedron Letters, Vol. 34, No. 21, pp 3401-3404, 1993; G. Shapiro and B. Gomez-Lor, J. Organic Chemistry, Vol. 59, pp 5524-5526, 1994).

In more detail, the reaction may be conveniently effected by initially preparing a solution of 1-methylimidazole in a solvent such as tetrahydrofuran, to which is added a portion of the $C_{4-6}$alkyllithium compound in a solvent such as n-hexane. The silyl halide is then added to the resulting reaction mixture, and a further portion of the $C_{4-6}$alkyllithium compound in a solvent such as n-hexane is also added. The compound of formula (IX) in a solvent such as tetrahydrofuran is then added to the reaction mixture, keeping the temperature between −78° C. and 0° C.

Another feature of the present invention are the compounds of formula (IX)

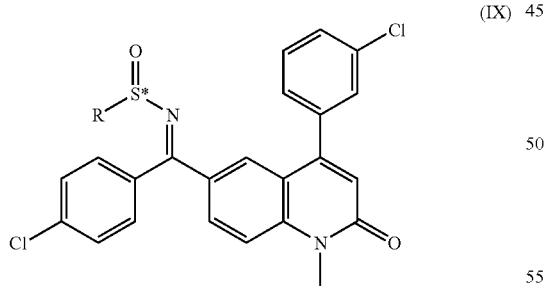

(IX)

and the stereochemically isomeric forms thereof wherein R is $C_{1-6}$alkyl or $C_{1-6}$alkylphenyl-.

Compounds of formula (IX) can be present as E and Z isomers which can rapidly interconvert.

Preferred compounds of formula (IX), are those compounds of formula (IX) wherein R is methylpropyl or methylphenyl, more preferably 2-methyl-2-propyl or methylphenyl. More preferred compounds of formula (IX) are compound 13, i.e. N-[(4-chlorophenyl)((4-(3-chlorophenyl)-1-methyl-1H-quinolin-2-one)-6-yl)methylene]-2-methyl-2-propanesulfinamide, or compound 14, i.e. N-[(4chlorophenyl)((4-(3-chlorophenyl)-1-methyl-1H-quinolin-2-one)-6-yl)methylene]-p-toluenesulfinamide.

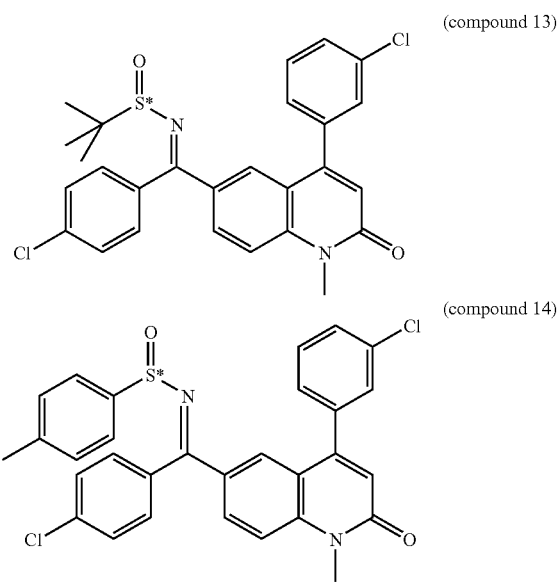

(compound 13)

(compound 14)

The most preferred compound of formula (IX) is compound 15, i.e. N-[(4-chlorophenyl)((4-(3-chlorophenyl)-1-methyl-1H-quinolin-2-one)-6-yl)methylene]-2-methyl-2-propanesulfinamide [S(R)].

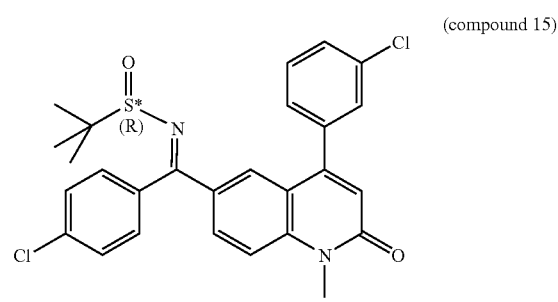

(compound 15)

The compound of formula (IX) wherein R is $C_{1-6}$alkyl or $C_{1-6}$alkylphenyl-, can be made by addition of a chiral sulfinamide of formula (X) wherein R is $C_{1-6}$alkyl or $C_{1-6}$alkylphenyl-, in the presence of titanium (IV) ethoxide and a suitable solvent, such as dichloromethane or tetrahydrofuran.

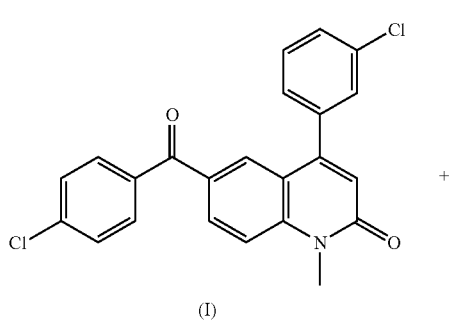

(I)

-continued

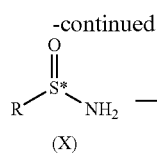

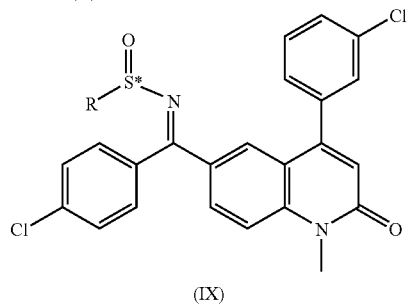

R in the chiral sulfinamide of formula (X) is preferable 2-methyl-2-propanyl or 4-methylphenyl. The most preferred chiral sulfinamide of formula (X) is (R)-(+)-2-methyl-2-propane-sulfinamide.

The term chiral sulfinamide of formula (X) means the compound of formula (X), wherein the enantiomeric excess is 40% or higher, preferably higher than 60%, more preferably higher than 80%, most preferably higher than 94%.

Another feature of the present invention is a compound of formula (VIII)

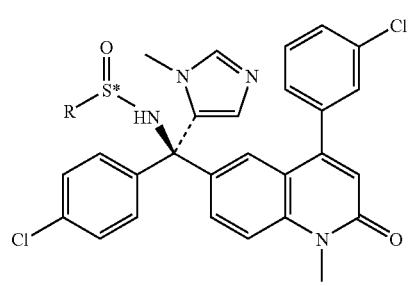

and the stereochemically isomeric forms thereof wherein R is $C_{1-6}$alkyl or $C_{1-6}$alkylphenyl-.

Preferred compounds of formula (VIII) are those compounds wherein R is methylpropyl. A more preferred compound of formula (VIII) is compound 16, i.e. (R)-N-[(4-chlorophenyl)((4-(3-chlorophenyl)-1-methyl-1H-quinoline-2-one)-6-yl)(1-methyl-1H-imidazole-5-yl)methyl]-2-methyl-2-propanesulfinamide [S(R)].

(compound 16)

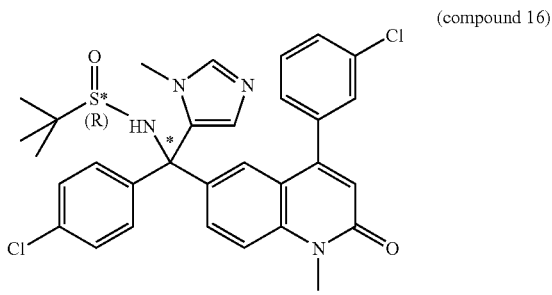

The most preferred compound of formula (VIII) is compound 18 (diastereomer (B) of compound 16).

(compound 18)

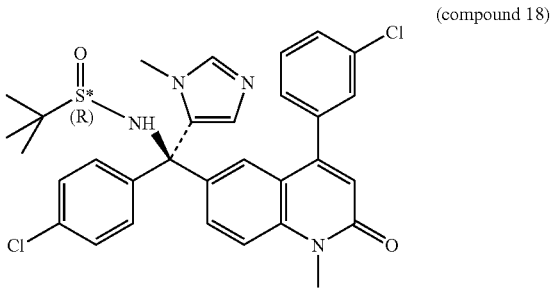

Compounds of formula (VIII) can be converted into the compound of formula (V) under acidic conditions, for example by addition of hydrochloric acid, in a suitable solvent, for example isopropanol or methanol, at a suitable temperature, for example room temperature.

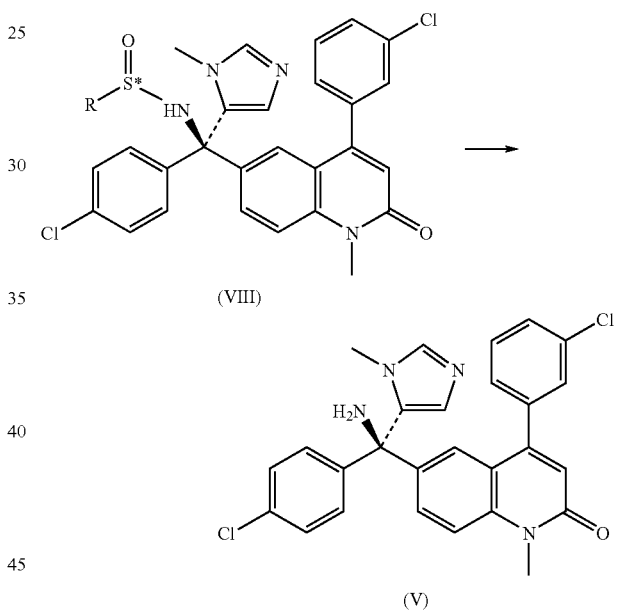

The pharmaceutically acceptable acid addition salts as mentioned hereinabove are meant to comprise the therapeutically active non-toxic acid and non-toxic base addition salt forms which the compounds of formula (VIII) and (IX) are able to form. The compounds of formula (VIII) and (IX) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The terms acid addition salt also comprise the hydrates and the solvent addition forms which the compounds of formula (VIII) and (IX) are able to form. Examples of such forms are e.g. hydrates, alcoholates and the like.

The term stereochemically isomeric forms of compounds of formula (VIII) and (IX), as used hereinbefore, defines all possible compounds made up of the same atoms bonded by the same sequence of bonds but having different three-dimensional structures which are not interchangeable, which the compounds of formula (VIII) and (IX) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (VIII) and (IX) both in pure form or in admixture with each other are intended to be embraced within the scope of the present invention.

The following examples illustrate the present invention.

Hereinafter "DCM" means dichloromethane, "EtOAc" means ethyl acetate, "MeOH" means methanol, "Ti(OEt)$_4$" means titanium (IV) ethoxide, and "THF" means tetrahydrofuran.

A. Preparation of Intermediates

EXAMPLE A.1 a) Preparation of N-[(4-chlorophenyl)((4-(3-chlorophenyl)-1-methyl-1H-quinolin-2-one)-6-yl)methylene]-2-methyl-2-propanesulfinamide [S(R)] (compound 15)

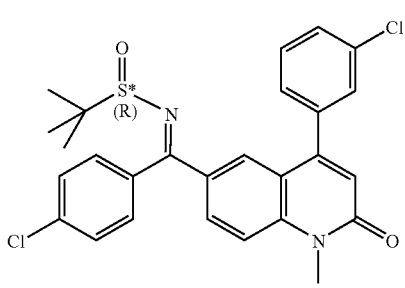

(compound 15)

Ti(OEt)$_4$ (0.0122 mol) was added to a mixture of compound (I) (0.0024 mol) and (R)-(+)-2-methyl-2-propane-sulfinamide (0.0024 mol) in DCM (15 ml). The mixture was stirred and refluxed for 4 days, then cooled to room temperature. Ice water was added. The mixture was filtered over celite. Celite was washed with DCM. The organic layer was extracted with saturated sodium chloride. The organic layer was separated, dried (MgSO4), filtered, and the solvent was evaporated. This fraction was purified by column chromatography over silica gel (40 μm) (eluent: DCM/MeOH 98/2). The pure fractions were collected and the solvent was evaporated, yielding 0.95 g of compound 15_(76%), melting point: 115° C.

b) Preparation of (R)—N-[(4-chlorophenyl)((4-(3-chlorophenyl)-1-methyl-1H-quinoline-2-one)-6-yl) (1-methyl-1H-imidazole-5-yl)methyl]-2-methyl-2-propanesulfinamide [S(R)] (compound 16)

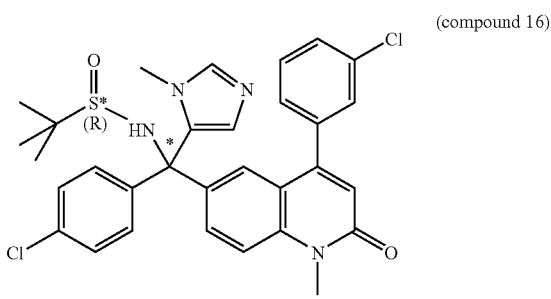

(compound 16)

n-Butyllithium (1.34 ml, 0.002 mol) was added dropwise at −70° C. to a mixture of 1-methylimidazole (0.0021 mol) in THF (4.5 ml). The mixture was stirred at −70° C. for 15 minutes. Triethylsilyl chloride (0.0021 mol) was added. The mixture was stirred at −70° C. for 15 minutes. n-Butyllithium (1.34 ml, 0.0021 mol) was added dropwise. The mixture was stirred at −70° C. for 15 minutes. A solution of compound 15 (0.0019 mol) in THF (5.5 ml) was added. The mixture was stirred at −70° C. for 45 minutes, poured out into ice water and extracted with EtOAc. The organic layer was separated, dried (MgSO4), filtered, and the solvent was evaporated. The residue was purified by column chromatography over silica gel (15-40 μm)(eluent: DCM/MeOH/NH$_4$OH 95/5/0.5), yielding 0.59 g (52%) of compound 16, diastereomeric excess 24%.

c) Preparation of the (B)-diastereomer (compound 18) of compound 16

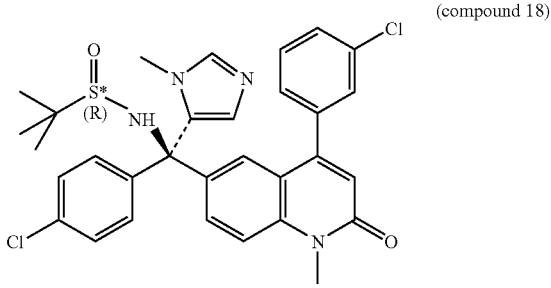

(compound 18)

Compound 16 was purified by column chromatography over silica gel (15-40 μm) (eluent: DCM/MeOH/NH$_4$OH 95/5/0.5). Two fractions were collected and the solvent was evaporated, yielding 0.304 g diastereomer (B) (compound 18) (27%), melting point 174° C.

EXAMPLE A.2 a) Preparation of N-[(4-chlorophenyl)((4-(3-chlorophenyl)-1-methyl-1H-quinolin-2-one)-6-yl)methylene]4-methylphenylsulfinamidesulfinamide [S(S)] (compound 17)

(compound 17)

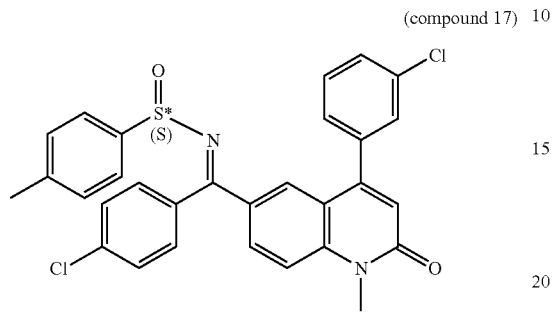

Ti(OEt)₄ (0.0122 mol) was added to a mixture of compound (I) (0.0123 mol) and (S)-(+)-p-toluenesulfinamide (0.0123 mol) in DCM (80 ml). The mixture was stirred and refluxed for 4 days, then cooled to room temperature. Satured sodium chloride was added. The mixture was filtered over celite. Celite was washed with DCM. The organic layer was separated, dried (MgSO4), filtered, and the solvent was evaporated. A fraction was purified by column chromatography over silica gel (40 μm) (eluent: DCM/MeOH 98/2). The fractions were collected and the solvent was evaporated, yielding 0.65 g of pure compound 17.

The pure compound N-[(4-chlorophenyl)((4-(3-chlorophenyl)-1-methyl-1H-quinolin-2-one)-6-yl)methylene]-2-methyl-2-propanesulfinamide [S(R)] can be obtained in an analogues way.

B. Preparation of Final Compounds

EXAMPLE B.1 a) Preparation of Compound (V)

compound (V)

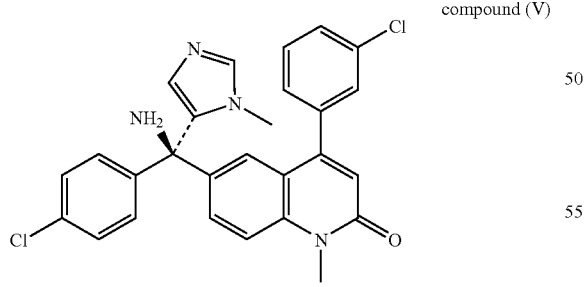

Hydrochloric acid in isopropanol was added to a solution of compound 16 (0.00003 mol) in methanol (0.7 ml). The mixture was stirred at room temperature for 30 minutes. The mixture was added to potassium carbonate (10%) on ice. The organic layer was separated, washed with a solution of saturated sodium chloride, dried (MgSO₄), filtered, and evaporated giving 0.017 g (100%) of compound (V), enantiomeric excess 22%, content of compound (II)<1%.

The invention claimed is:

1. A process for the preparation of the following compound

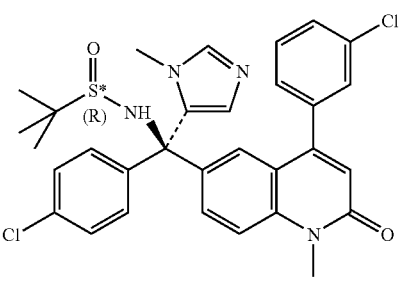

in diastereomeric excess of 20% or higher, comprising reacting the compound

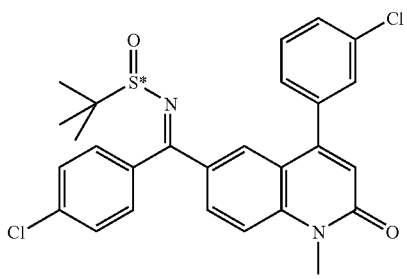

with a 1-imidazole product formed by reacting 1-imidazole with n-butyl-lithium or n-hexyl-lithium, reacting the resulting product with triethylsilyl halide or tri-iso-butylsilyl halide and reacting the resulting product with n-butyl-lithium or n-hexyl-lithium.

2. A process as claimed in claim 1 wherein the halide in the triethylsilyl halide or tri-iso-butylsilyl halide is chloride.

3. A process of claim 1 in which the reaction with the 1-imidazole product is effected in a tetrahydrofuran solvent, the reaction time is 45 minutes, and the reaction is performed at a temperature between −78° C. and 0° C.

4. A process as claimed in claim 1 wherein the compound

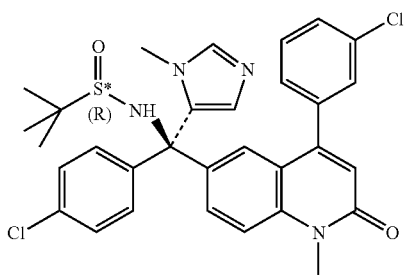

is subsequently purified from the other diastereomer by crystallization or chromatography.

5. A process as claimed in claim 1 wherein the compound

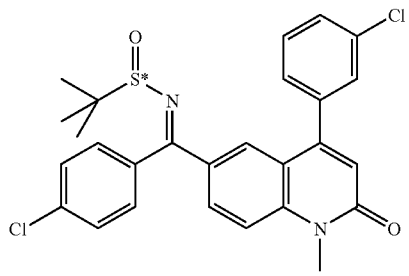

is prepared by addition of (R)-(+)-2-methyl-2-propane-sulfinamide of the following formula

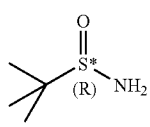

to the compound of formula

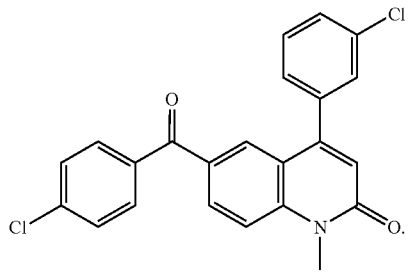

6. A process as claimed in claim 1 wherein the compound of the following formula

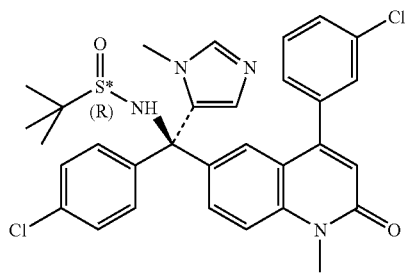

is converted into the compound

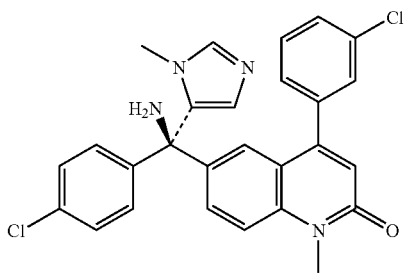

under acidic conditions, in a suitable solvent, at a suitable temperature.

7. The compound of the formula

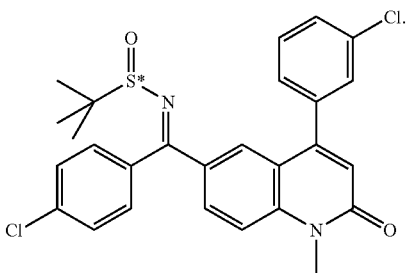

8. The compound of formula

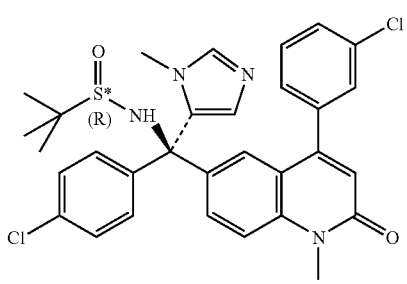

in a diastereomeric excess of 20% or higher.

* * * * *

UNITED STATES PATENT AND TRADEMARK OFFICE
CERTIFICATE OF CORRECTION

PATENT NO. : 7,524,961 B2
APPLICATION NO. : 11/568415
DATED : April 28, 2009
INVENTOR(S) : Filliers et al.

Page 1 of 1

It is certified that error appears in the above-identified patent and that said Letters Patent is hereby corrected as shown below:

In claim 6, Column 18, the formula was incorrectly printed. Please see the correct formula below:

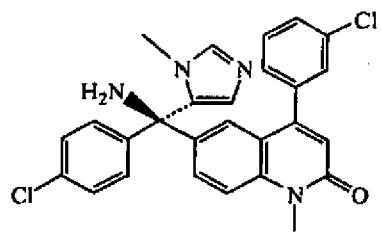

Signed and Sealed this

Eighth Day of December, 2009

David J. Kappos
*Director of the United States Patent and Trademark Office*